United States Patent [19]
Pambianchi et al.

[11] Patent Number: 5,662,672
[45] Date of Patent: Sep. 2, 1997

[54] SINGLE USE, BI-DIRECTIONAL LINEAR MOTION LANCET

[75] Inventors: Michael S. Pambianchi, New Milford, Conn.; Dominick F. Grube, Ogdensburg, N.J.

[73] Assignee: Array Medical, Inc., Bridgewater, N.J.

[21] Appl. No.: 653,712

[22] Filed: May 23, 1996

[51] Int. Cl.$^6$ .................................................. A61B 17/14
[52] U.S. Cl. .......................... 606/181; 606/182; 128/770
[58] Field of Search ................................ 606/181, 182, 606/183; 604/157; 128/770

[56] References Cited

U.S. PATENT DOCUMENTS

| | | |
|---|---|---|
| 3,760,809 | 9/1973 | Campbell, Jr. . |
| 3,902,475 | 9/1975 | Begg et al. . |
| 4,078,552 | 3/1978 | Chen et al. . |
| 4,230,118 | 10/1980 | Holman et al. . |
| 4,414,975 | 11/1983 | Ryder et al. . |
| 4,539,988 | 9/1985 | Shirley et al. . |
| 4,553,541 | 11/1985 | Burns . |
| 4,580,565 | 4/1986 | Cornell et al. . |
| 4,643,189 | 2/1987 | Mintz . |
| 4,715,374 | 12/1987 | Maggio . |
| 4,844,095 | 7/1989 | Chiodo et al. . |
| 4,889,117 | 12/1989 | Stevens . |
| 4,892,097 | 1/1990 | Ranalletta et al. . |
| 4,983,178 | 1/1991 | Schnell ............................. 606/181 |
| 4,990,154 | 2/1991 | Brown et al. . |
| 5,026,388 | 6/1991 | Ingalz . |
| 5,074,872 | 12/1991 | Brown et al. . |
| 5,100,427 | 3/1992 | Crossman et al. . |
| 5,152,775 | 10/1992 | Ruppert . |
| 5,314,441 | 5/1994 | Cusack et al. . |
| 5,366,469 | 11/1994 | Steg et al. . |
| 5,366,470 | 11/1994 | Ramel . |
| 5,395,388 | 3/1995 | Schraga . |
| 5,421,347 | 6/1995 | Enstrom . |
| 5,439,473 | 8/1995 | Jorgensen . |
| 5,476,474 | 12/1995 | Davis et al. . |
| 5,514,152 | 5/1996 | Smith ............................. 606/182 |

*Primary Examiner*—Michael Buiz
*Assistant Examiner*—Kevin Truong
*Attorney, Agent, or Firm*—Ralph T. Lilore

[57] ABSTRACT

There is described a skin piercing device which converts a longitudinal linear motion of a blade within the housing of the device into a vertical linear motion which, in consequence of the placement of a spring, restraints and stops in the device, results in the ejection of the blade out of the housing and into the patient's skin and back again into the housing in a rapid "in-out" fashion. The dimensions of the restraints and stops are individually controllable and, as a result, it is possible to achieve a length of cut which is independent of the depth of cut.

9 Claims, 2 Drawing Sheets

SINGLE USE, BI-DIRECTIONAL LINEAR MOTION LANCET

BACKGROUND OF INVENTION

This invention relates to lancet devices of the kind used to produce incisions in the skin for the purpose of releasing small amounts of blood therefrom.

The prior art is replete with cutting devices used to make small incisions in the finger or some other accessible tissue of the patient. A wide variety of lancet devices has been described, some of which have been commercialized. In general, they comprise cutting components located in a housing which conceals the cutting device and the actuating motion which causes the blade to be protected out of the housing and into the patient's tissue. Usually, the blade communicates with a restrained spring means and responds to the uncoiling action of the spring means upon release of the restraint. The blade then moves in a linear or a rotational motion through the housing and into the tissue site to be cut. Oftentimes, such devices are painful or inconvenient to use.

In the prior art, there exist many different designs for providing such incisions. Modern devices are usually designed for single-use, disposable operation and utilize a spring-loaded mechanism for accelerating the blade or needle through the course of its cutting motion. In general, three main types of lancet devices are encountered in the prior art. They may be classified as "stab", "slap", and "slice" devices.

The simplest of these is the "stab" group, to which the majority of prior art devices belongs. Devices of this group, exemplified by U.S. Pat. No. 4,889,117 issued on Dec. 26, 1989 to Stevens entitled DISPOSABLE LANCET and U.S. Pat. No. 4,553,541 issued to Burns entitled AUTOMATIC RETRACTABLE LANCET ASSEMBLY, employ a sharp, pointed needle or blade which is driven directly into the patient's skin with a puncturing action. The needle or blade may then be retracted back into its housing. Devices of this type have an advantage in their simplicity, though they cannot offer a completely controllable incision, nor do they attempt to address the needs of patients more susceptible to epidermal trauma, such as the elderly or the newborn.

Lancet devices of the "slap" group are similar in many ways to the "stab" group. For example, in U.S. Pat. No. 3,760,809 to Campbell, Jr. entitled SURGICAL LANCET HAVING CASING, a sharp blade is affixed to a flexible member inside the housing. In the starting position, this flexible member is bent at one end and hooked to the release mechanism at the roof of the housing. When activated, the energy stored in the flexible member is released, slapping the blade down through a sealed membrane and into the patient's skin. The incision produced is very similar to those produced by "stab" devices. Though they operate very quickly, both "stab" and "slap" devices produce an incision of nonreproduceable depth and can cause patient discomfort. Retracting the blade requires a complicated mechanism, or is not done at all in prior art devices of these types.

The third type of prior art device is the group characterized by blades which move primarily in a direction parallel to the skin of the patient, using a slicing motion to create an incision. In U.S. Pat. No. 5,314,441 to Cusack, et. al. entitled DISPOSABLE SLICING LANCET ASSEMBLY, a blade, sharpened only on one vertical edge, is attached to a fixed pivot point in the center of the housing. A torsional spring drives the rotating motion of the blade around this fixed pivot point, causing the blade to exit the housing, perform a slicing incision in the patient's skin, and then reenter the housing for the balance of its motion. Further, the path of the blade need not be purely circular; using an elongated slot in the blade, motion in the radial direction may also be accomplished. This allows the path of the blade to be specified precisely, by implementing a guide slot embossed on an interior wall of the housing. In U.S. Pat. No. 4,643,189 to Mintz entitled APPARATUS FOR IMPLEMENTING A STANDARDIZED SKIN INCISION, such a guide slot is used to create an incision of uniform length and depth for bleeding time applications.

The present invention belongs to the group of "slicing" lancet devices, and addresses the need for an even simpler, more painless incision method utilizing strictly linear blade motion.

SUMMARY OF THE INVENTION

In accordance with the present invention, there is provided a device which in its broad sense converts a longitudinal linear motion of a blade within the housing of a device into a vertical linear motion which in consequence of the placement of biasing means, restraints and stops in the device results in the ejection of the blade out of the housing and into the patient's skin and back again into the housing in a rapid "in-out" fashion. The dimensions of the restraints and stops are individually controllable and, as a result, it is possible to achieve a length of cut which is independent of the depth of cut.

The configuration of the blade is such that a slicing edge is presented in the direction of longitudinal movement of the blade point. When the blade's longitudinal movement through the device is converted to the perpendicular linear thrust as be discussed in more detailed below, the blade point pierces the skin in a vertical move and then continues in a longitudinal direction movement for a short duration causing a slicing of tissue. This is followed by a rapid withdrawal of the blade from the incision area as a result of certain restraints and stops provided in the housing of the device cooperating with the shape of the blade opposite the blade point. Stated another way, the slicing motion traverses only linear motion and it does so in two dimensions, one a longitudinal direction within the housing, and the other a perpendicular movement first piercing the patient's skin followed by another perpendicular motion as the blade retracts, all the while being under the influence of a longitudinal thrust.

Broadly, the device of the present invention comprises a generally elongated, housing having an internal channel, a cutting blade-holding assembly disposed within said channel and carrying a blade having a pointed end with a slicing edge for piercing and cutting tissue and an end opposite thereto, said blade disposed generally in a direction perpendicular to said channel, said blade and said assembly being movable in said channel between a cocked first retracted position, an extended piercing and cutting position, and a second retracted position wherein the second retracted position is downstream of the piercing position, biasing means in contact with said holding assembly and disposed to move said assembly in a longitudinal direction through said channel from said first cocked retracted position into said extended piercing position and then into said second retracted position, stop means associated with said housing, ejection, and retraction means associated with said end opposite said pointed end of said blade and with said holding assembly and said housing and whereby when said holding assembly is moved upon its longitudinal pathway said stop means cooperate with said ejection means and retraction means to convert the longitudinal movement of the blade into transverse movement of said blade out of said housing and into skin piercing position, followed by retraction of said blade back into said housing.

In tracing the pathway of the blade point, beginning with the movement caused by the release of a biasing means from its energy storing state, one would find that in the longitudinal pathway, the blade-holding assembly carrying the blade first moves longitudinally through a generally elongated channel in the housing from its first retracted resting position. When the blade point reaches slot means in the housing at the area used for piercing the patient (piercing slot means), the configuration of the end opposite the blade point enables cooperation with a restraint or stop (housing stop) placed in registration with said piercing slot means in the housing. This configuration is in the form of an angled leading edge, such as is provided by an arrowhead, which engages the housing stop, i.e. the end of the slot. This causes a pushing down of the blade into the housing and a continuing longitudinal slicing movement therethrough as the biasing means continues its expansion action. The blade is thus ejected through the slot means out of the housing in a direction generally perpendicular to the first longitudinal motion, piercing the skin in that perpendicular direction. The depth of the piercing and the subsequent cut is a function of the length of the entire blade from the piercing point to the end of the angled leading edge. It continues a slight distance longitudinally in a straight line in the patient's tissue as determined by the length of the opposing housing stop as it encounters the angled cutting edge and then retracts into a second slot means perpendicularly in the housing to a second retracted position by reason of the angled leading edge of the end opposite the blade point having reached the slot and being urged upwardly therein by the release of pressure on the restraining means in said holding assembly.

Generally, the elements of the device which permit the blade to traverse the path described are facilitated by the first slot means of the housing itself which permit the blade to remain retracted as it moves through the housing, ejection means comprising the wall and the opposing slot provided in the path of the point to permit ejection of the knife point to pierce the skin, resilient or biasing means in the holding assembly in contact with the blade holder and engaging the knife to urge it down into the piercing slot upon deformation and to retract it upon release of the deformation. Movement of the blade is facilitated by biasing means located longitudinally which move the blade-holding assembly through the housing. The blade-holding assembly itself has resilient means such as a spring, a foam, or a rubbery elastomeric material controlling the location, placement, and movement of the blade within the assembly.

DETAILED DESCRIPTION OF THE DRAWINGS AND PREFERRED EMBODIMENTS

Figure 1:
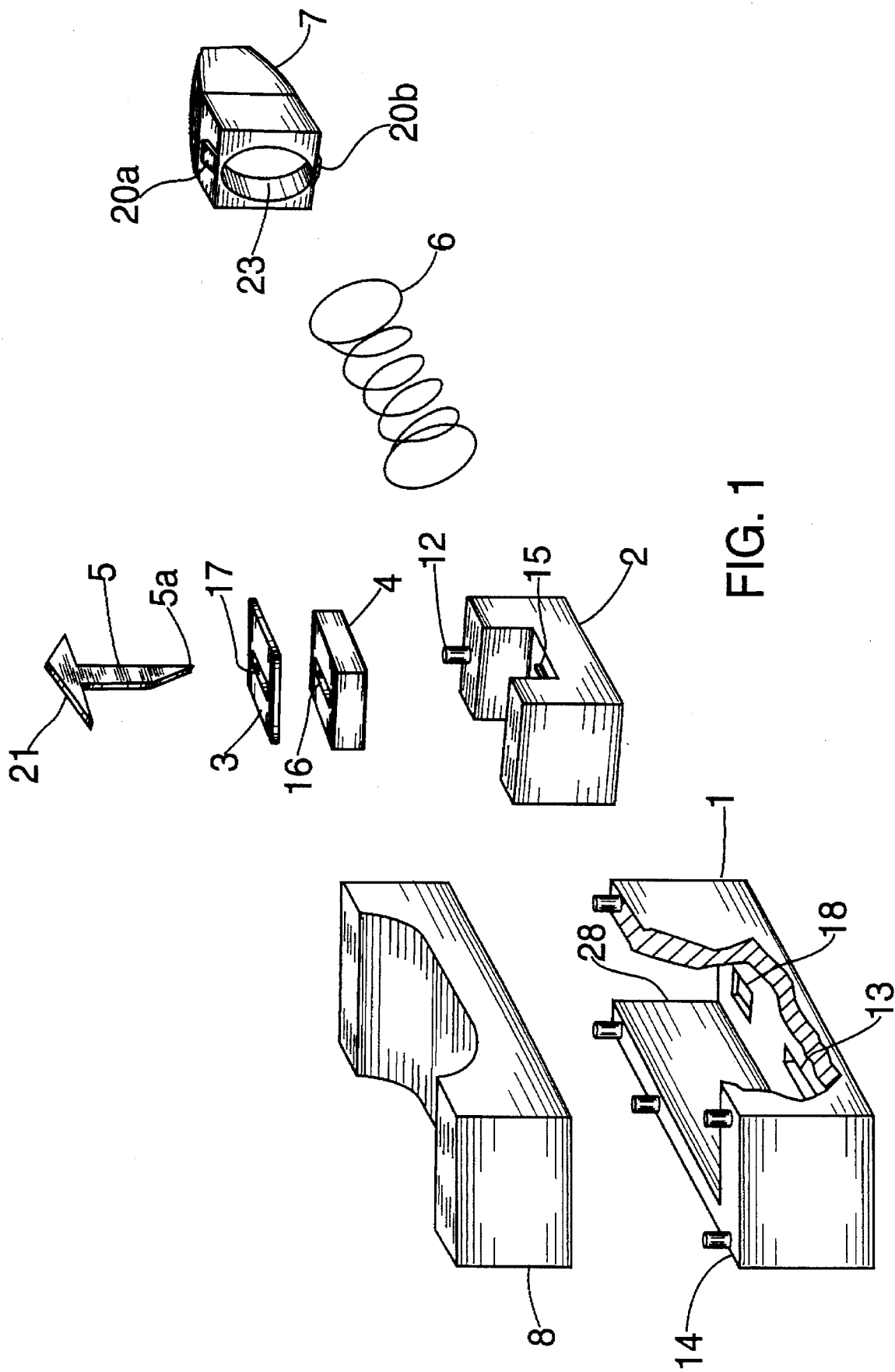
FIG. 1 is an exploded side view of the lancet device of the invention.

The device of FIG. 1 comprises an elongated slot 13 in the bottom surface of the housing 1 intended to be placed into contact with the skin to be pierced. When the device is activated, a cutting blade 5 will be ejected from the elongated slot 13, cut the patient's skin, and retract from the incision area back into the housing.

The cutting blade 5 having blade point 5a resides in the slot 17 of the cutting blade retaining means 3, an optional, but preferred component. The cutting blade retaining means 3 has a slot 17 from its top to its bottom surfaces and may be any shape consistent with the shape of the housing and the device itself. The angled leading edge head 21 (shown as part of the cutting blade 5) rests in slot 9a and sits against the top surface of the cutting blade retaining means 3. The leading edge 21 instead of terminating in the point of an arrowhead, may simply continue in a straight line colinear with the longitudinal direction of the housing or it may drop off into the main length of the blade after the desired length of the angled edge is traversed. As will be seen, head 21 constitutes part of the ejection means when in communication with stop 10 and part of the retraction means when stop 10 is traversed and slot 9b) is reached. The cutting blade is held in the slot 16 running through the top and bottom surfaces of the resilient biasing means 4. As noted previously, the material used for the resilient biasing means 4 may be generally an elastomeric, resilient, "rubbery" material such as a silicone or other plastic polymeric material, rubber, a foam or spring means. Preferably, a rubbery material is used. Its purpose is to deform when the bottom of leading edge head 21 is pressed against blade retaining means 3 which in turn presses against resilient means 4 to allow point 5a to protrude from slot 13 and to force the blade to retract when the pressure on leading edge head 21 is released.

The cutting blade 5 resides in slot 15 of the blade carrier 2. The cutting blade 5 is designed not to protrude from the slot 15 in the blade carrier 2, when in the assembled state at rest. The blade carrier 2 generally conforms in shape to the channel with a cut-out in its top surface, and has a slot 15 through the inner top surface of the cut-out to the bottom surface. A shear pin 12 is provided on carrier 2 protruding from its top surface. (One may also be provided on the bottom surface to provide stability.) The subassembly thus comprises cutting blade 5, cutting blade retaining means 3, resilient means 4, and blade carrier 2.

Figure 2:
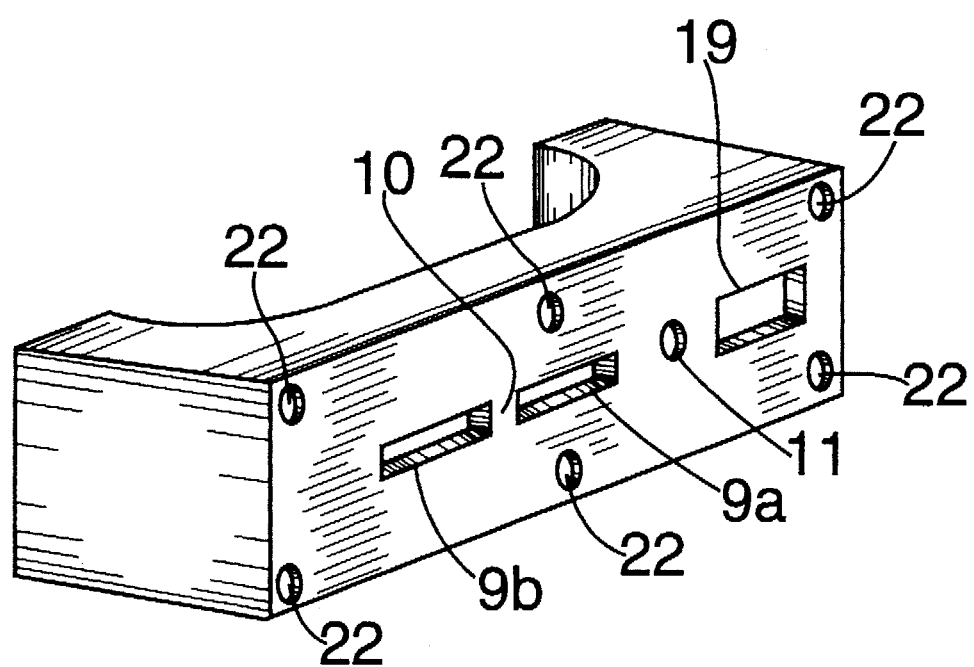
FIG. 2 is perspective view of the bottom of the top cover of FIG. 1.

The subassembly described above is placed against the bottom surface of the top cover 8 so that the shear pin 12 of the blade carrier 2 is accepted by the counterbore 11 of the top cover 8 (refer to FIG. 2). The top cover 8 of FIG. 2 has a cut-out in its top surface, counterbores 11 and 22 and slots 9 and 19 in its bottom surface. The housing 1 mates with the top cover 8 so that the protruding pins 14 provided in the top surface of the housing press fit into the counterbores 22 of the top cover 8. Housing 1, as shown, has a bottom surface, three sides, one open end, and an open top. Housing 1 may, of course, be of a different shape such as a cylinder, for example. Elongated slots 13 and 18 are provided in its bottom surface. Spring biasing means 6 is placed into the open end of the mated housing 1 and top cover 8 and rests against the end surface of the blade carrier 2. The final assembly step is to press the end cap 7 in the slot 18 of the housing 1 and the slot 19 of the top cover 8. The wedge-shaped protrusions 20a and 20b set forth in slots 19 and 18, respectively, and prevent the end cap 7 from being pushed out of the device by the linear spring biasing means 6 and hold the linear spring biasing means 6 in a semi-compressed state. The counterbore 23 in the end cap 7 accepts the linear spring biasing means 6 acting as a guide.

The function of the device is unique when compared to prior art devices. In use, the device is placed against the patient's skin with the elongated slot 13 of the housing 1 making contact with the skin. The operator of the device holds it between the thumb and index finger and uses the forefinger to press on the end cap 7. This pressure causes the shear pin 12 in the blade carrier 2 to break thereby acting as a triggering means for the expansion of the linear spring biasing means 6. The blade carrier 2 is then propelled longitudinally by the force of the linear spring biasing means 6. The leading edge 21 of the cutting blade 5 (which blade originally has its point residing in slot 9a), upon movement will contact the common section of wall 10 which acts as a stop between the two colinear slots 9a and 9b in the bottom surface of the top cover 8. This common section of wall 10, cooperating with lead edge 21, will force the cutting blade 5 transversely allowing it to eject first from the slot 15 in the blade carrier 2 and then from the slot 13 in the housing 1. The resulting deformation of the resilient means 4 will allow the "give" required for blade protrusion. The blade will make an incision in the skin and then be retracted back into the device when the barrier created by the common section of wall 10 is overcome by the leading edge head 21 of the cutting blade 5. The force required to retract the cutting blade 5 back into the device through slot 9b) is provided by the receive means 4. The device cannot be reset once the shear pin 12 has been broken making the device fully disposable with no chance of re-use.

In another embodiment, instead of providing peg 12 in the carrier to releasably secure the carrier to cover 8, a slot can be provided transversely through the carrier 2 located in registration with matching slots in the walls of housing 1 to receive means, such as a peg bolt or restraining rod which then act as the securing means. The carrier can then be projected into motion by either pushing or pulling the restraining rod out of the carrier. When in place, the carrier 2 would be in a cocked first retracted position. Release of the peg causes expansion of the spring means 6 triggering the required longitudinal movement of carrier 2. In addition, a biasing means 6 can be positioned in front of carrier 2 and appropriately connected and secured such that release of the carrier from the biasing means in an extended position causes a "pull" on said carrier.

There are a variety of modifications that may be employed within the scope and spirit of the invention as will be apparent to those skilled in the art. All such modifications are intended to be encompassed within the scope of the invention.

We claim:

1. A disposable lancet device comprising:
   a) generally elongated housing having an internal channel,
   b) a cutting blade-holding assembly disposed within said channel and carrying a blade having a pointed end and a slicing edge at said end for piercing and slicing tissue and an end opposite thereto, said blade disposed generally in a direction perpendicular to said channel, said blade and said assembly being movable longitudinally in said channel from a cocked first retracted position to and through an extended piercing position, and then to a second retracted position wherein the second retracted position is downstream of the piercing position,
   c) biasing means in contact with said holding assembly and disposed to move said assembly in a longitudinal direction through said channel from said first cocked retracted position into said extended piercing position and into said second retracted position,
   d) stop means associated with said housing, and ejection and retraction means associated with said end opposite said pointed end of said blade and with said holding assembly and with said housing, whereby when said holding assembly is moved upon its longitudinal pathway said stop means cooperate with said ejection means and retraction means to convert the longitudinal movement of the blade into transverse movement of said blade out of said housing and into skin piercing position, followed by retraction of said blade back into said housing.

2. The device of claim 1 wherein said slicing edge is oriented in a slicing configuration relative to said tissue and said end opposite said blade comprises an angled leading edge head oriented in the same plane as said slicing edge.

3. The device of claim 2 wherein the blade is held in a holding assembly comprising a resilient means capable of being compressed upon exertion of pressure thereon and of returning to substantially its original position when said pressure is released.

4. The device of claim 3 wherein the housing comprises a first elongated slot to accommodate at least a portion of said angled leading edge head when said device is in a cocked first retracted state, a second elongated slot downstream of said first slot and colinear therewith to accommodate at least a portion of said head in a second retracted state and a wall between said first and said second slots and colinear therewith, said wall being engagable with the angled leading edge of said head to induce a transverse component of motion to said blade when said head of said blade moves longitudinally and encounters said wall.

5. The device of claim 4 wherein said housing comprises an elongated blade point slot opposite to and in registration with said wall to accommodate the blade piercing point when said head encounters said wall and moves transversely.

6. The device of claim 5 wherein said blade point slot is greater in length in the longitudinal direction than the length of said wall in the same direction.

7. The device of claim 6 wherein the biasing means is spring activated.

8. The device of claim 7 wherein the spring biasing means is located upstream of the direction of longitudinal movement of said blade-holding assembly and said spring is its energy storing state when the assembly is in the cocked first retracted state.

9. The device of claim 8 wherein said resilient means of said holding assembly is an elastomeric material.

* * * * *